United States Patent [19]

Hoch

[11] 4,412,548

[45] Nov. 1, 1983

[54] MULTIPLE SAMPLE NEEDLE ASSEMBLY

[75] Inventor: Louis Hoch, Nutley, N.J.

[73] Assignee: Becton Dickinson and Company, Paramus, N.J.

[21] Appl. No.: 288,640

[22] Filed: Jul. 30, 1981

[51] Int. Cl.³ .............................................. A61B 5/14
[52] U.S. Cl. .................................................. 128/764
[58] Field of Search ......................... 128/760, 763–768

[56] References Cited

U.S. PATENT DOCUMENTS 4,166,450 9/1979 Abramson .......................... 128/764

Primary Examiner—Kyle L. Howell
Assistant Examiner—John C. Hanley

[57] ABSTRACT

A multiple sample needle assembly useful in collecting fluid samples from a source includes a housing with a chamber therein. A first cannula, in fluid communication with the chamber, is provided for insertion into a fluid source. A second cannula is movably positioned in the housing and communicates with the chamber. A flow mechanism inside the chamber prevents fluid from flowing from the chamber into the second cannula. This flow mechanism is operatively responsive to inward movement of the second cannula to allow fluid to flow from the chamber into the second cannula for collection therefrom.

8 Claims, 5 Drawing Figures

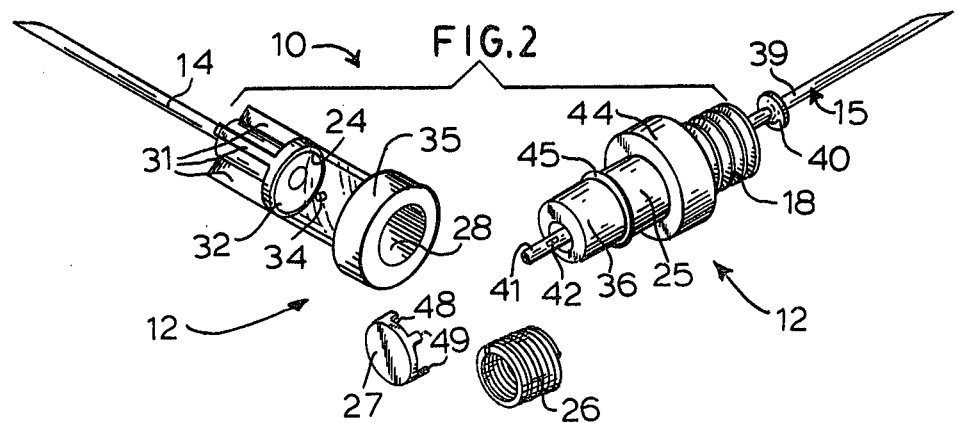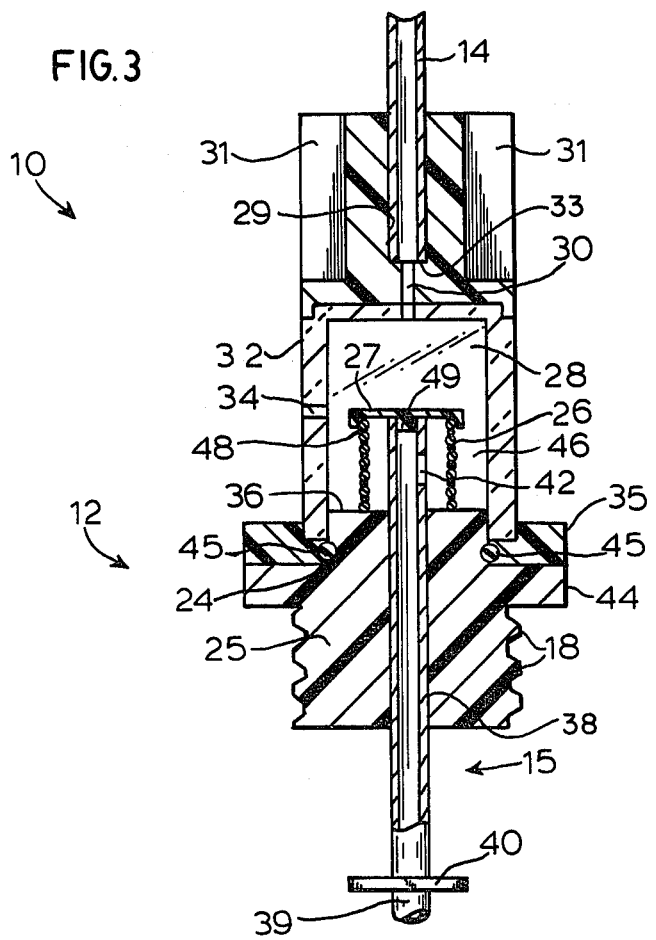

MULTIPLE SAMPLE NEEDLE ASSEMBLY

BACKGROUND OF THE INVENTION

1. Field of the Invention

The present invention relates to a needle assembly for collecting fluid such as blood from a patient, and more particularly, concerns a needle assembly for collecting multiple samples of blood from a patient into evacuated tubes without leaking blood while the tubes are being changed, and with a provision for indicating the entry of the needle assembly into the vein of the patient.

2. Description of the Prior Art

It is now standard practice to collect multiple samples of fluid, such as blood, from a patient in a single procedure. Once the needle is inserted into the vein of the patient, successive evacuated blood collection tubes are inserted into a holder which is connected to the needle and is adapted to receive these evacuated tubes therein. As each filled tube is removed from the holder, the needle remains inserted into the patient's vein. Various valves are now in use which prevent blood from flowing out of the holder during the time between removal of the filled tube and insertion of the next evacuated tube for collection of the subsequent sample. Elastomeric sleeves over an interior needle commonly serve this valve purpose. It is appreciated that, while the known valves for multiple sample needle assemblies perform satisfactorily, different ways are being sought to provide improvements in these devices.

U.S. Pat. Nos. 4,166,450; 4,099,520; 3,557,778; and 3,528,404 disclose representative blood sampling devices through which the flow of blood can be controlled during the collection of multiple samples.

In addition, it is also desirable to provide a mechanism whereby the user of a multiple sample needle assembly can be informed when the intravenous needle has penetrated the vein of the patient. Many times in collecting blood from a patient it is difficult to locate the vein or for other reasons blood flow into the collection device is minimal. In these instances, it becomes most advantageous to be able to make a quick determination that entry into the vein has been made and that blood is flowing into the needle assembly. Once this determination has been made and vein entry indeed accomplished, the evacuated blood collection container can then be inserted into the collection assembly in accordance with these well known techniques of collecting multiple blood samples during a single collection procedure.

One of the problems which arises during the venipuncture step concerns the pocket of air which is found in various needle assemblies useful for multiple sample blood collections. When venipuncture is made, and the evacuated blood collection container is not yet attached to the opposite end of the needle structure, blood cannot always flow into the needle assembly because of this pocket of air, which, under normal atmospheric conditions, remains inside the needle assembly. Accordingly, even though vein entry may have been accomplished, the blood may not move through the intravenous needle into the collection assembly under tourniquet pressure until the evacuated blood collection container is attached, whereupon the vacuum source causes sufficient draw through the needle assembly. It is thus desirable to provide a mechanism for purging the air from inside the needle assembly so that blood can readily flow into the assembly as it displaces the air.

SUMMARY OF THE INVENTION

The multiple sample needle assembly of the present invention is useful in collecting fluid samples from a source. This assembly includes a housing with a chamber therein. A first cannula is in fluid communication with the chamber and is adapted for insertion into a fluid source. A second cannula is movably positioned in the housing and communicates with the chamber. Means inside the chamber prevents fluid from flowing from the chamber into the second cannula. This means is operatively responsive to inward movement of the second cannula to allow fluid to flow from the chamber into the second cannula for collection therefrom.

In a preferred embodiment of the present invention, the housing includes a forward end, a rearward end and the chamber within. The housing is translucent at least around the chamber so that the chamber is viewable by a user of the assembly. In this embodiment, the first cannula is adapted for insertion into a patient for collecting blood or other bodily fluids, and extends outwardly from the forward end of the housing. The second cannula is slidably positioned in the rearward end of the housing and has an exterior portion extending outwardly and an interior portion extending inwardly into the chamber with an access opening providing fluid communication between this interior portion of the second cannula and the chamber. A tightly wound coil spring is inside the chamber surrounding the interior portion of the second cannula. This spring is affixed to the rearward end of the housing and includes a cap sealing the interior cross-sectional end of the spring closed. In addition, the cap is connected to the second cannula. Thus, the tightly wound coils of the spring and the cap serve to prevent blood which is in the chamber from entering into the access opening. When a force is applied to the second cannula, it slides inwardly to thereby expand the spring and produce a space between the coils. Blood in the chamber then flows through these spaces into the access opening of the second cannula for collection of the blood therefrom. Upon removal of the applied force, the second cannula slides outwardly to tightly compress the spring and prevent blood from flowing through the access opening.

From the structural standpoint, there are a number of elements of the present invention which are notably different from prior art multiple sample needle assemblies. For instance, the blood flow control means of the present invention is operable by virtue of a mechanically applied force, rather than the reliance upon a pressure differential to open and close a blood flow control valve. Therefore, positive mechanical control of the blood flow control mechanism is assured. Furthermore, the blood flow control mechanism of the present invention is located inside the housing so that it is self-protected during storage, transportation and handling during use. In addition, the components comprising the present invention can be fabricated straightforwardly and inexpensively, so that the needle assembly can be readily disposable. Other advantages of the present invention are offered as well.

BRIEF DESCRIPTION OF THE DRAWINGS

FIG. 2 is an exploded perspective view illustrating the components of the preferred multiple sample needle assembly of the present invention;

FIG. 3 is an enlarged cross-sectional view taken along line 3—3 of FIG. 1;

DETAILED DESCRIPTION

Figure 1:
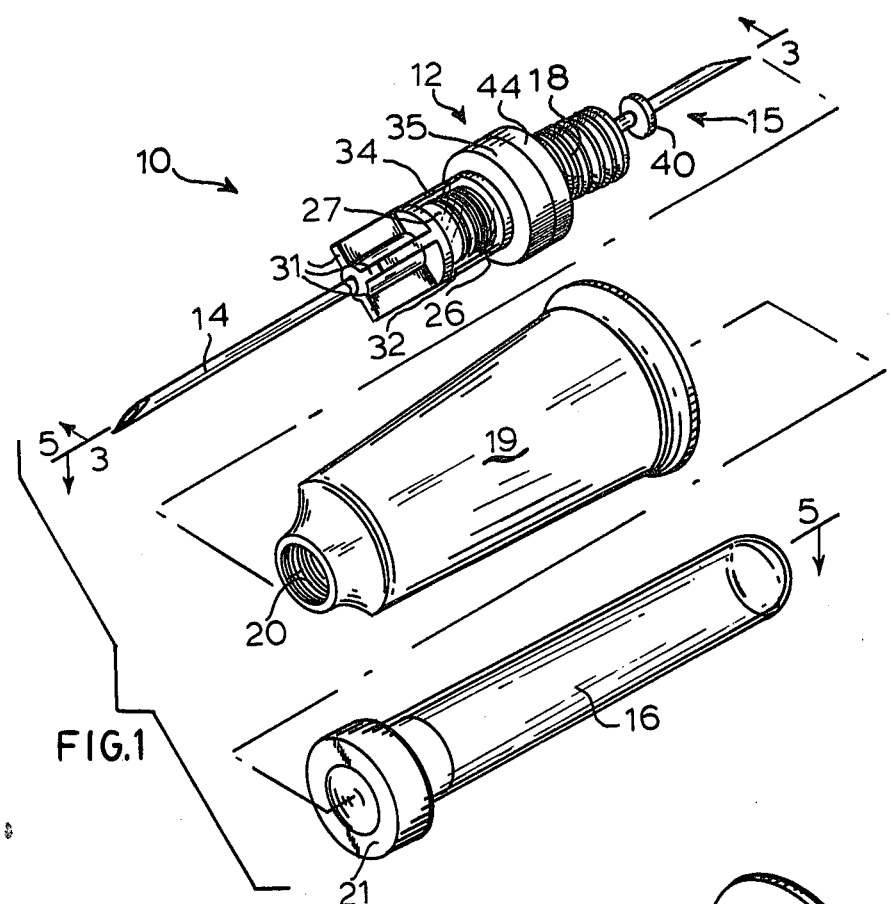
FIG. 1 is an exploded perspective view illustrating the preferred multiple sample needle assembly, a holder for an evacuated container and an evacuated blood collection container for use in obtaining blood samples from a patient.

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Turning to the drawings, particularly to FIG. 1, there is illustrated the preferred embodiment of a multiple sample needle assembly 10. The basic external components of needle assembly 10 include a housing 12, a first needle cannula 14 adapted for insertion into a patient and a second needle cannula 15 at the opposite end of housing 12, the second needle cannula adapted for penetration of an evacuated container 16 for collection of a blood sample. Housing 12 includes a threaded portion 18 adjacent second cannula 15 onto which a container holder 19 is threaded by internal mating threads 20 at the forward end of the holder. Evacuated container 16 slides into holder 19 so that second needle cannula 15 can penetrate the penetrable stopper 21 at the forward end of the evacuated container. These general aspects of multiple sample blood collections in this type of structure are well known to those skilled in this art.

In FIGS. 2 and 3, the detailed construction of needle assembly 10 is illustrated. Housing 12 has a forward end 24 and a rearward end 25, these ends being preferably separable in order to place coil spring 26 and sealing cap 27 in their proper positions inside the housing. Forward end 24 is preferably cylindrically shaped and has a larger bore extending into and partially through its body. This bore serves as a chamber 28 inside the housing when the forward and rearward ends are mated. At the other end of this section, a smaller bore 29 is included which is generally sized to slidably fit needle cannula 14 therein. In this embodiment being described, smaller bore 29 does not extend completely through forward end 24 to communicate with chamber 28. However, a still smaller diameter channel 30 interconnects these two bores so that there is fluid communication from needle cannula 14 into chamber 28. At the junction between bore 29 and channel 30 a shoulder 33 is formed. Needle cannula 14 abuts against this shoulder 33 for proper positioning. Once the needle cannula is in position it can be suitably affixed such as by adhesive means or the like. It is appreciated that the presence of channel 30 is not essential to the structure of this forward end of the housing, but is merely a preferable element. However, it will be appreciated that the diameter of channel 30 can be varied to provide a regulation of the fluid flow rate which flows therethrough.

Forward end 24 of the housing also includes a number of longitudinal ribs 31 surrounding the outwardly extending cannula. A needle shield (not shown) generally covers the outwardly extending needle cannula and includes mating internal ribs within. The mating ribs between the needle shield and needle assembly allow the user to facilitate the insertion or removal of the needle assembly into the tube holder. The outer portion 32 of the forward end surrounding chamber 28 is preferably smooth and translucent or transparent so that a user of this assembly can view the interior of the housing. In many situations, it may be preferable to make the entire forward end, and even possibly the rearward end, out of translucent or transparent material for ease of manufacture and to minimize the different types of materials which may be used in this assembly. Translucent rigid plastic is the most desirable material for inclusion in this assembly. Various sealed windows, ports or other means for a user to view the contents of the chamber are within the purview of this invention. It is preferable that such window or port be sealed so that any blood which enters chamber 28 upon the needle entering the vein will not escape from this assembly.

An air vent hole 34 extends through wall section 32 around the chamber. Vent hole 34 is sized so that air can readily pass therethrough but blood or fluids will not. To this end, a hydrophobic membrane may be placed against the inside wall of chamber 28 covering hole 34, of such thickness and pore rating so that air can pass therethrough but that blood will be prevented from so passing. While air vent opening 34 is illustrated in this embodiment as being through wall portion 32, this is merely a preferred location. As long as there is communication between chamber 28 and the outside atmosphere for air to pass, such a vent passage could be located elsewhere in this assembly. For instance, such a passage may be included, by appropriate design, in cap 27 or through spring 26, once again, providing that there is air communication between chamber 28 and the atmosphere surrounding the assembly. Also, it should be kept in mind that the translucent nature of wall portion 32 and the inclusion of vent opening 34 are to provide a visual indicator to the user of this assembly that blood has entered chamber 28 upon needle cannula 14 making entry into the vein of the patient. These elements of the present invention which provide this feature are preferably included herein, and are not essential as far as the operation of a multiple sample needle assembly.

Forward end 24 also includes an annular flange 35 which serves to provide a surface for joining the two portions of the housing together upon assembly. Once again, suitable fastening means, such as adhesives or the like may be used to secure the two portions of the housing together.

Rearward end 25 includes a short protruding portion 36, generally cylindrically shaped and sized to fit within chamber 28 of the forward end, generally for alignment purposes during assembly of the components. At the opposite side of this rearward end, external threads 18 are provided as previously mentioned as a connection mechanism to the tube holder. A bore 38 extends through the rearward end of the housing and is sized to accept the diameter of second needle cannula 15 in a slidable fit therein. This second needle cannula includes an exterior portion 39 extending outwardly from the rearward end, including an annular ring 40 around its periphery. This ring, or similar protuberance or the like, is located on exterior portion 39 so that it is spaced a short distance from the rearward end of the housing where the threads terminate. Second cannula 15 also includes an interior portion 41 extending inwardly into the chamber. In addition to second cannula 15 being hollow completely therethrough, a side access opening 42 extends through interior portion 41 to provide fluid communication between this interior portion of the second cannula and the chamber. In this arrangement, second cannula 15 is free to slide within bore 38 in the rearward end of the housing. An annular flange 44 is provided to cooperate with flange 35 in joining the two ends of the housing together. To assure proper fluid flow through the housing, an annular, elastomeric ring 45 may be included in this embodiment around protruding portion 36. Upon assembling forward end and rearward ends together, with spring 26 and cap 27 placed in their proper positions, respective flanges 35 and 44 are secured together by appropriate fastening means, such as adhesives or the like.

Spring 26 is compressed under normal conditions in a tightly wound configuration. Its coils contact each other in a sufficiently tight arrangement to substantially prevent blood or other fluids from passing between the coils. When assembled inside chamber 38, coil spring 26 is positioned against protruding portion 36 of the rearward end of the housing. It is substantially concentrically oriented so that the spring surrounds interior portion 41 of the second cannula. Also, the surrounding spring covers side access opening 42. Spring 26 is preferably sized so that there is an annular clearance 46 between the spring and the inside wall of translucent portion 32. This spring is sealingly affixed to protruding portion 36, using adhesives or the like, which also prevents blood or other fluids from passing under the spring.

In order to completely seal off access opening 42 from the flow of blood, cap 27 is sealingly connected to the opposite end of the spring, specifically across the interior cross-sectional end thereof. Cap 27 may include hooks 48 to tuck under the last coil of the spring to assist in this sealing connection. Adhesives or the like may also be employed to facilitate this connection. Cap 27 also includes a centrally located protruding hub 49 which is inserted into the hollow passage of interior portion 41 of the second cannula. Either by interference fit or the utilization of adhesives or the like, interior portion 41 is thereby connected to cap 27 in conjunction with hub 49. As a result of this arrangement, i.e., the tightly wound contacting coils of spring 26, the sealing engagement of spring 26 to the rearward end of the housing and the sealing connection of cap 27 to the spring, blood or other fluids is prevented from passing from the chamber into the second cannula. With respect to spring 26, its coils may include a wrap of soft material, such as nylon or the like, which will assist in providing fluid-tight contact between adjacent coils. Other variations may be employed as well to assure that fluid will not pass through the coil spring when the spring is in the compressed condition.

Figure 4:
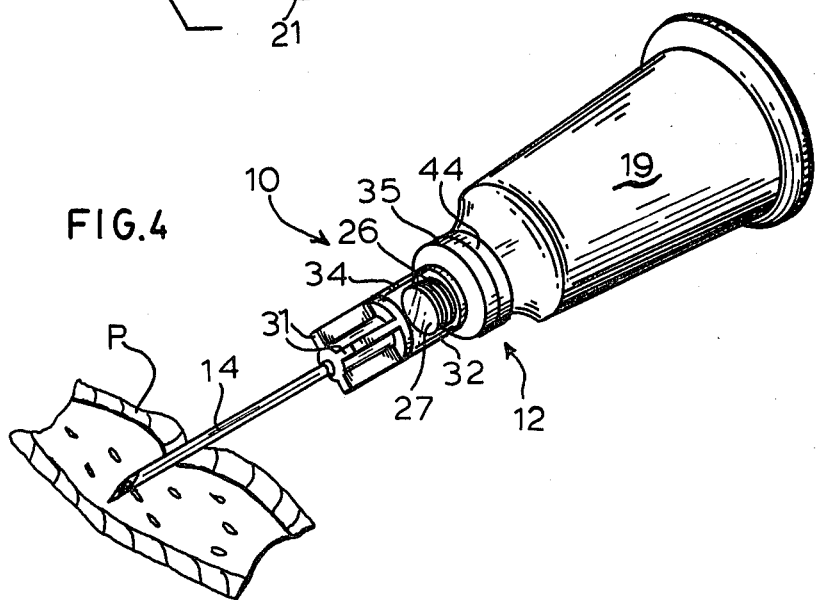
FIG. 4 is a perspective view of the needle assembly connected to a holder inserted into a patient so that a user can view same for indication of vein entry.

Referring now to FIG. 4, the preferred needle assembly 10 is illustrated connected to a multiple sample holder 19. Cannula 14 is shown inserted into a patient P during the venipuncture procedure. At this time, spring 26 remains in the tightly compressed condition as illustrated in FIG. 3. The pressure inside the patient's vein will force blood through cannula 14 into forward end 24 of the housing and then into chamber 28. Any air which may be initially inside chamber 28 will then be forced out by the entering blood through air vent 34, which is permeable to air, but substantially impermeable to blood. Blood will then fill chamber 28 including annular space 46 around spring 26. With at least portion 32 of the forward end being translucent, the user of this needle assembly can then view the blood as it enters chamber 28 and remains there while spring 26 is in the compressed condition. As soon as the user sees the blood in chamber 28, it serves as an indication that vein entry has been made. Conversely, if the user does not see blood flow into the chamber, it can safely be assumed that vein entry has not been accomplished. With this feature, the user does not have to attach an evacuated blood collection container until vein entry indication has been received.

Figure 5:
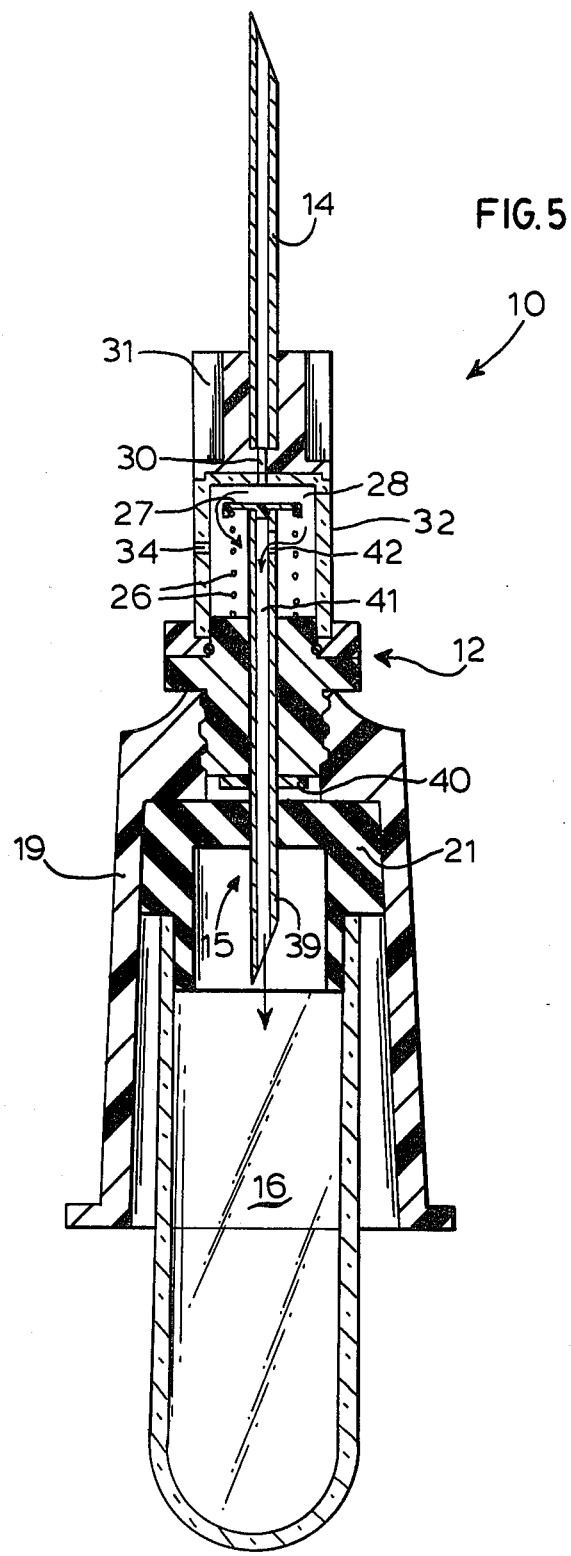
FIG. 5 is a cross-sectional view taken along line 5—5 of FIG. 1 with the components in an assembled condition as they would appear during use.

FIG. 5 illustrates the evacuated blood collection container 16 inserted into holder 19 so that penetrable stopper 21 is penetrated by exterior portion 39 of the second cannula. In sliding container 16 into holder 19, the forward end of stopper 21 will initially make contact with the leading point of exterior portion 39 of the cannula. Inasmuch as this cannula is slidable, further inward sliding movement of the blood collection container will urge this second cannula inwardly into the needle assembly. Once the second cannula penetrates penetrable stopper 21, there may be sufficient friction to maintain the second cannula in its inwardly displaced position. However, to assure that the second cannula maintains this inward displacement, penetrable stopper 21 abuts against annular ring 40, thereby moving this ring into engagement with the end of the housing as the second cannula slides inwardly.

When second cannula 15 moves inwardly, the connection between the interior portion of this cannula, cap 27 and spring 26 causes the spring to expand as more clearly seen in FIG. 5. Once spring 26 expands, the individual coils become spaced apart, and thus are no longer in intimate contact with each other. Accordingly, blood inside chamber 28 is free to flow through the spaces between adjacent coils of spring. Blood then flows into side access opening 42 whereupon it is delivered from second cannula 15 into blood collection container 16. The evacuated condition of the blood collection container also assists in drawing the blood from the chamber, through the access opening and into the second cannula.

As soon as the force of the stopper against the annular ring, or friction force of the penetrable stopper against the second cannula, is removed, such as withdrawing the filled blood collection container, spring 26 once again becomes compressed. As described above, in this compressed condition adjacent coils of the spring contact each other and substantially prevent the flow of blood through the spring. This effectively serves as a control valve mechanism to stop blood from leaking out of the second cannula particularly during the time when the user is changing blood collection containers during the multiple sampling procedure. Of course, during the multiple sampling procedure, cannula 14 remains inserted into the vein of the patient. Inasmuch as spring 26 is normally biased to compress, removal of the applied force causes the spring to compress and the second cannula to slide outwardly to its original, static position.

While the present invention has been described with a spring serving as the flow control mechanism, it is appreciated that other displacement-sensitive components may also be utilized within the present invention.

For example, one alternative which readily comes to mind is an extensible elastomeric tube which includes a self-sealing slit through a peripheral wall. If such an elastomeric tube were to replace the coil spring, inward movement of the second cannula would expand the elastomeric tube thereby opening the slit to a wide aperture. Blood would then flow through this wide aperture, into and through such elastomeric tubing. As soon as the applied force is released, such elastomeric tubing would compress, and the self-sealing slit would once again become closed to prevent the flow of blood into the tubing. Other such arrangements also fall within the scope and spirit of the present invention.

Thus, the multiple sample needle assembly of the present invention provides a mechanism to prevent leakage of blood or other fluids from the assembly, particularly during the changing of blood collection containers during the multiple sampling procedure. Furthermore, the preferred embodiment hereof is so structured to provide a visual indicator to the user when vein entry has been made. These aforementioned features contribute to the efficient use of this type of assembly in the multiple sample collection procedure.

What is claimed is:

1. A multiple sample needle assembly for determining vein entry when collecting blood samples from a patient comprising:
    a housing having a forward end, a rearward end and a chamber within, said housing being translucent at least around the chamber so that said chamber is viewable by a user of said assembly;
    a first cannula in fluid communication with said chamber extending outwardly from said forward end adapted for insertion into a patient;
    a second cannula slidably positioned in said rearward end and having a first end portion extending outwardly from said rearward end and a second end portion extending inwardly into said chamber with an access opening extending through the wall of said second end portion and providing fluid communication between said second end portion and said chamber; and
    a tightly wound coil spring inside said chamber surrounding the interior portion of said second cannula, said spring being sealingly affixed to the rearward end of said housing; a cap extending over and sealing the end of said spring opposite said end affixed to said rearward end of said housing, said cap being connected to said second cannula, said tightly wound coils and said cap adapted to prevent blood in said chamber from entering into said access opening in the compressed position of said spring, said second cannula adapted to slide inwardly into said chamber under the influence of a force applied to said first end portion to thereby expand said spring and produce spaces between said coils so that blood in said chamber flows through said spaces into said access opening for collection through said second cannula, said spring adapted to become tightly compressed upon removal of said force, said compressing movement sliding said second cannula outwardly from said chamber, and said compressed spring preventing blood from flowing through said access opening.

2. The assembly of claim 1 wherein said air vent is adapted to pass air therethrough but prevent blood from flowing therethrough.

3. The assembly of claim 1 wherein said first end portion of said second cannula is adapted for penetration of an evacuated container for collection of a blood sample.

4. The assembly of claim 1 wherein the entire housing is translucent.

5. The assembly of claim 1 wherein the first end portion of said second cannula includes an annular ring around its periphery to aid movement of said second cannula inwardly during use.

6. The assembly of claim 1 wherein the housing includes means for connecting a holder for an evacuated container.

7. The assembly of claim 8 which further includes a holder for an evacuated container connected to said housing.

8. A multiple sample needle assembly for determining vein entry when collecting blood samples from a patient into an evacuated container comprising:
    a translucent housing having a forward end, a rearward end and a chamber within, said chamber being viewable by a user of said assembly;
    an air vent providing fluid communication between said chamber and atmosphere adapted to pass air, but not blood, therethrough;
    a first cannula in fluid communication with said chamber extending outwardly from said forward end adapted for insertion into a patient;
    a second cannula slidably positioned in said rearward end and having a first end portion extending outwardly from said rearward end with an annular ring around its periphery, and a second end portion extending inwardly into said chamber with a side access opening extending through the wall of said second end portion providing fluid communication between said second end portion and said chamber; and
    a tightly wound coil spring inside said chamber surrounding said second end portion of said second cannula, said spring being sealingly affixed to the rearward end of said housing; a cap extending over and sealing the end of said spring opposite said end affixed to said rearward end of said housing, said cap being connected to said second cannula, said tightly wound coils and said cap adapted to prevent blood in said chamber from entering into said access opening in the compressed position of said spring, said second cannula adapted to slide inwardly into said chamber under the influence of a force applied to said first end portion and said annular ring to thereby expand said spring and produce spaces between said coils so that blood in said chamber flows through said spaces and into said access opening for collection through said second cannula, said spring adapted to become tightly compressed upon removal of said force, said compressing movement sliding said second cannula outwardly from said chamber, and said compressed spring preventing blood from flowing through said access opening.

* * * * *